US012765777B2

(12) United States Patent
Asaoka

(10) Patent No.: US 12,765,777 B2
(45) Date of Patent: Oct. 20, 2026

(54) IMAGE GENERATION DEVICE, ENDOSCOPIC SYSTEM, AND IMAGE GENERATION METHOD

(71) Applicant: OLYMPUS MEDICAL SYSTEMS CORP., Tokyo (JP)

(72) Inventor: Nobuyoshi Asaoka, Ageo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 127 days.

(21) Appl. No.: 18/367,625

(22) Filed: Sep. 13, 2023

(65) Prior Publication Data

US 2023/0414105 A1 Dec. 28, 2023

Related U.S. Application Data

(63) Continuation of application No. PCT/JP2021/010527, filed on Mar. 16, 2021.

(51) Int. Cl.
*A61B 5/00* (2006.01)
*A61B 8/00* (2006.01)
*A61B 8/12* (2006.01)

(52) U.S. Cl.
CPC .............. *A61B 5/0095* (2013.01); *A61B 8/12* (2013.01); *A61B 8/4477* (2013.01)

(58) Field of Classification Search
CPC ....... A61B 1/0051; A61B 1/05; A61B 1/0669; A61B 1/07; A61B 5/0035; A61B 5/0095; A61B 5/7267; A61B 8/0891; A61B 8/12; A61B 8/4416; A61B 8/4477; A61B 8/5261
See application file for complete search history.

(56) References Cited

U.S. PATENT DOCUMENTS

2018/0368696 A1* 12/2018 Abe ..................... A61B 5/0095
2019/0076119 A1* 3/2019 Yang ........................ A61B 1/07
2019/0090853 A1* 3/2019 Masaki ................ A61B 8/5207

FOREIGN PATENT DOCUMENTS

JP 2015-150238 A 8/2015
JP 2018-089406 A 6/2018
JP 2019-107084 A 7/2019
WO WO-2018207713 A1 * 11/2018 ........... A61B 5/0095

OTHER PUBLICATIONS

Joon-Mo Yang et al., "Simultaneous functional photoacoustic and ultrasonic endoscopy of internal organs in vivo," Jul. 15, 2012, Nature Medicine, 18, pp. 1297-1302 (Year: 2012).*
International Search Report dated Jun. 8, 2021 received in PCT/JP2021/010527.

* cited by examiner

*Primary Examiner* — Michael J Carey
*Assistant Examiner* — Maria Christina Talty
(74) *Attorney, Agent, or Firm* — Scully, Scott, Murphy & Presser, P.C.

(57) ABSTRACT

An image generation device that generates an image of a subject includes a processor configured to generate an ultrasonic image based on a reflected ultrasound signal, generate a photoacoustic image based on a photoacoustic wave signal, and generate an estimated photoacoustic image based on the photoacoustic image and the ultrasonic image.

20 Claims, 10 Drawing Sheets

IMAGE GENERATION DEVICE, ENDOSCOPIC SYSTEM, AND IMAGE GENERATION METHOD

CROSS-REFERENCE TO RELATED APPLICATIONS

The present application is a continuation application based on PCT Patent Application No. PCT/JP2021/010527, filed on Mar. 16, 2021, the entire content of which is hereby incorporated by reference.

BACKGROUND

Technical Field

The present invention relates to an image generation device, an endoscopic system, and an image generation method.

Description of the Background

Conventionally, photoacoustic imaging, which uses the photoacoustic effect to image a cross section of a living body, is known. Photoacoustic imaging detects photoacoustic waves (pressure waves) induced by irradiating a living body with light under certain conditions, and generates a photoacoustic image, which is a cross-sectional image of the living body, based on the photoacoustic waves.

Photoacoustic imaging makes it easy to visualize the blood vessels of a living body in a photoacoustic image. Photoacoustic imaging can generate cross-sectional images of living organisms with higher resolution and contrast than ultrasound imaging that uses ultrasound echoes. Furthermore, photoacoustic imaging can obtain functional information, such as blood oxygen concentration, in addition to morphological information. On the other hand, in photoacoustic imaging, the living body absorbs the energy of the irradiated light, and the absorbed energy induces photoacoustic waves. In photoacoustic imaging, it is difficult to visualize a metal treatment instrument or the like that does not absorb light in a photoacoustic image.

Japanese Unexamined Patent Applications, First Publication No. 2019-107084, No. 2015-150238, and No. 2018-089406 describe an apparatus for observing a living body by combining photoacoustic observation by photoacoustic imaging and ultrasonic observation by ultrasonic imaging.

In the apparatus described in the above Patent Applications, since the amount of information on the photoacoustic wave to be detected in photoacoustic imaging is enormous, it takes a certain amount of time to generate a photoacoustic image from the detected photoacoustic waves by signal processing. The time required to generate a photoacoustic image by photoacoustic imaging is long compared to that required to generate an ultrasonic image by ultrasound imaging. Therefore, when observing a photoacoustic image and an ultrasonic image simultaneously, the photoacoustic image is delayed compared to the ultrasonic image.

SUMMARY

The present invention provides an image generation device, an endoscopic system, and an image generation method that can reduce the delay of photoacoustic images in photoacoustic imaging.

An image generation device according to a first aspect of the present invention is an image generation device that generates an image of a subject, including a processor configured to generate an ultrasonic image based on a reflected ultrasound signal, generate a photoacoustic image based on a photoacoustic wave signal, and generate an estimated photoacoustic image based on the photoacoustic image and the ultrasonic image.

According to the image generation device, endoscopic system, and image generation method of the present invention, the delay of photoacoustic images in photoacoustic imaging can be reduced.

EMBODIMENTS

First Embodiment

An endoscopic system 100 according to a first embodiment of the present invention will be described with reference to FIGS. 1 to 7.

[Endoscopic System 100]

Figure 1:
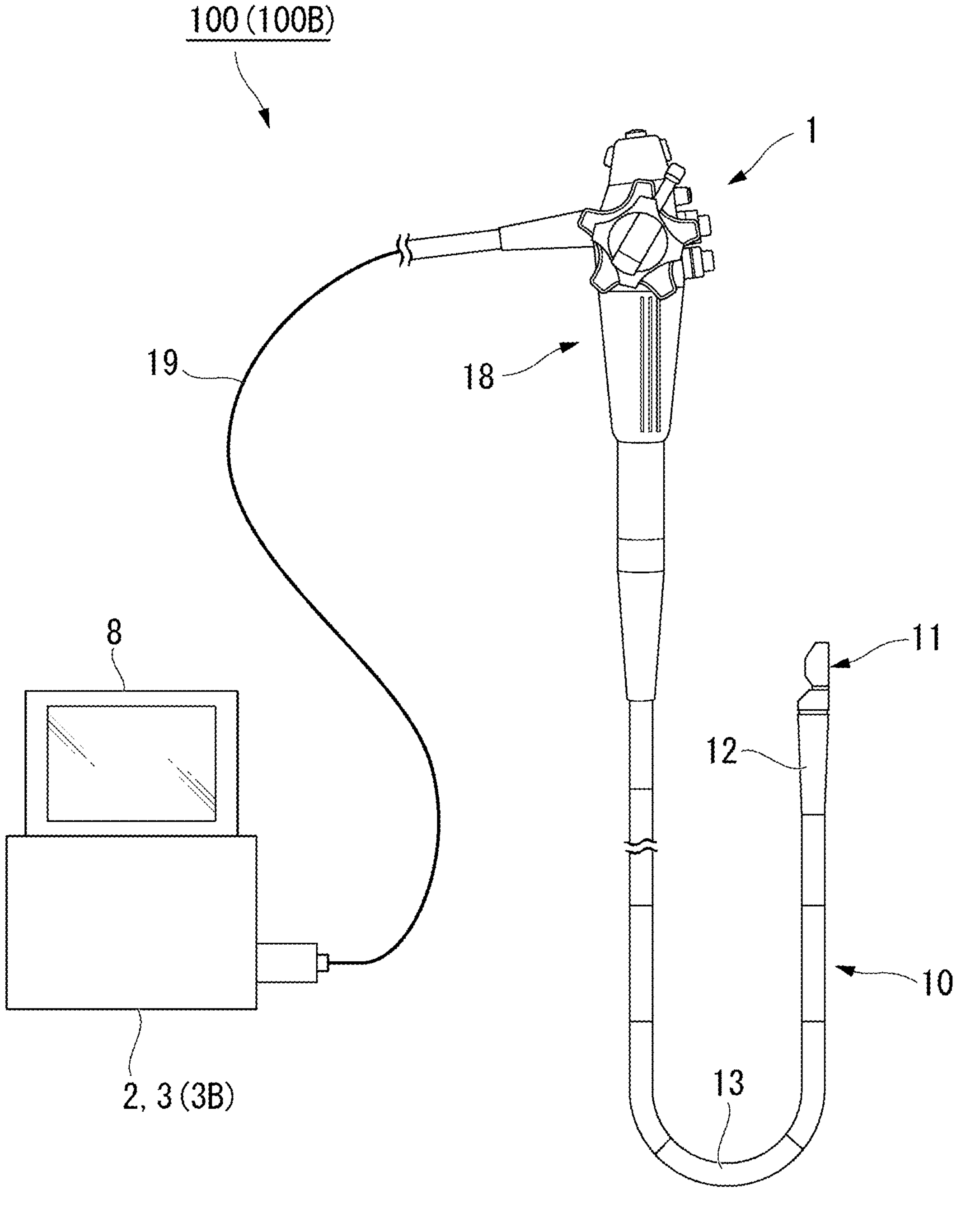
FIG. 1 is a diagram showing an endoscopic system according to a first embodiment.

FIG. 1 is a diagram showing the endoscopic system 100.

The endoscopic system is a system that can perform photoacoustic observation, ultrasonic observation, and optical observation of a subject (living body). The endoscopic system 100 includes an ultrasonic endoscope 1, a control device 2, an image generation device 3, and a display device 8. The display device 8 displays an image generated by the ultrasonic endoscope 1, various information about the endoscopic system 100, and the like.

[Ultrasound Endoscope 1]

The ultrasonic endoscope 1 includes an elongated insertion portion 10 to be inserted into the body, an operation portion 18 connected to the proximal end of the insertion portion 10, and a universal cord 19 extending from the operation portion 18.

The insertion portion 10 has a distal end rigid portion 11, a bendable bending portion 12, and flexible tube portion 13 that is a thin, long and flexible. The distal end rigid portion 11, the bending portion 12, and the flexible tube portion 13 are connected in order from the distal end side. The flexible tube portion 13 is connected to the operation portion 18.

Figure 2:
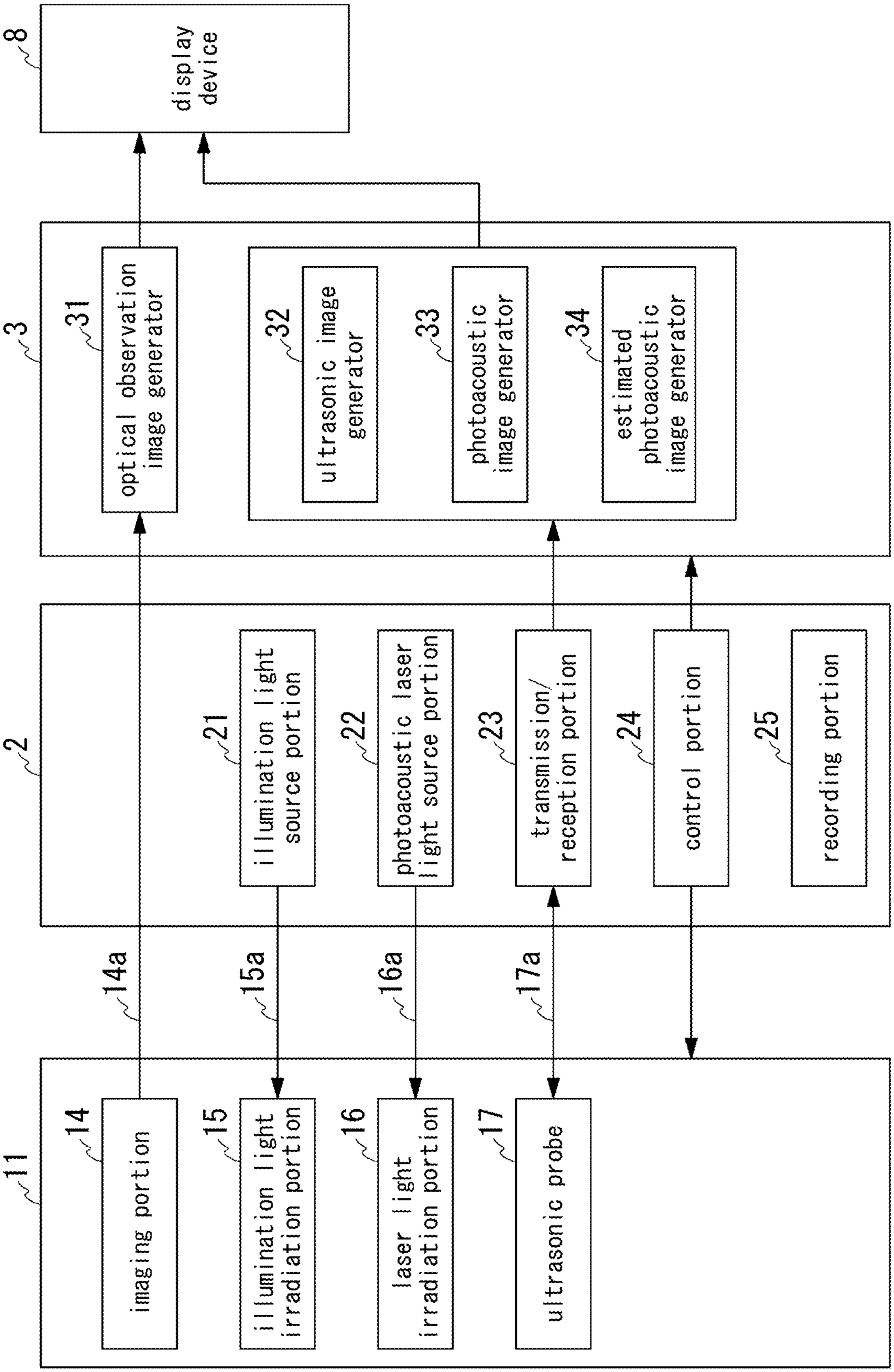
FIG. 2 is a functional block diagram of the endoscopic system.

FIG. 2 is a functional block diagram of the endoscopic system.

The distal end rigid portion 11 has an imaging portion 14, an illumination light irradiation portion 15, a laser light irradiation portion 16, and an ultrasonic probe 17.

The imaging portion 14 has an optical system and an imaging element such as a CMOS image sensor. The imaging portion 14 images a subject and generates an imaging signal. The imaging signal is transmitted to the image generation device 3 via a signal cable 14*a*.

The illumination light irradiation portion 15 irradiates the subject with the illumination light transmitted by a fiber cable 15*a*. The fiber cable 15*a* is inserted through the insertion portion 10, the operation portion 18, and the universal cord 19 to connect the illumination light irradiation portion 15 and the control device 2.

The laser light irradiation portion 16 emits photoacoustic laser light transmitted by a fiber cable 16*a*. The fiber cable 16*a* is inserted through the insertion portion 10, the operation portion 18, and the universal cord 19 to connect the laser beam irradiation portion 16 and the control device 2.

The ultrasonic probe (probe) 17 generates ultrasonic waves. The ultrasonic probe 17 also receives photoacoustic waves and ultrasonic echoes and converts them into electric signals. The converted electric signals are transmitted to the control device 2 via a signal cable 17*a*.

The ultrasonic probe 17 is an electroacoustic transducer in which a plurality of ultrasonic transducers are regularly arranged on a substrate. Each ultrasonic transducer has a piezoelectric element, an acoustic matching layer, an acoustic lens, and a backing layer. The ultrasonic probe 17 is appropriately selected from known electroacoustic conversion mechanisms such as those described in Japanese Unexamined Patent Application, First Publication No. 2015-150238.

The operation portion 18 accepts operations for the ultrasonic endoscope 1. The universal cord 19 connects the operation portion 18 and the control device 2.

[Control Device 2]

The control device 2 is a device that controls the endoscopic system 100 as a whole. The control device 2 includes an illumination light source portion 21, a photoacoustic laser light source portion 22, a transmission/reception portion 23, a control portion 24, and a recording portion 25.

The illumination light source portion 21 supplies illumination light emitted by the illumination light irradiation portion 15 via the fiber cable 15*a*. The illumination light source portion 21 has, for example, a halogen lamp or an LED.

The photoacoustic laser light source portion 22 generates a laser beam that produces a photoacoustic effect when the subject is irradiated, and makes the laser beam enter the fiber cable 16*a*. In the following description, the laser light for generating the photoacoustic effect generated by the photoacoustic laser light source portion 22 is referred to as photoacoustic laser light regardless of the wavelength. A photoacoustic wave (pressure wave) is induced by irradiating a subject with photoacoustic laser light.

The transmission/reception portion 23 drives the ultrasonic probe 17 to generate ultrasonic waves. The ultrasonic probe 17 receives ultrasonic echoes generated by reflection of the transmitted ultrasonic waves on a subject. The transmission/reception portion 23 receives an electric signal (hereinafter referred to as a “reflected ultrasonic signal”) obtained by converting an ultrasonic echo from the ultrasonic probe 17 and outputs the signal to the image generation device 3. The transmission/reception portion 23 also receives an electric signal (hereinafter referred to as “photoacoustic wave signal”) converted from a photoacoustic wave from the ultrasound probe 17 and outputs the signal to the image generation device 3.

The control portion 24 is a program-executable processing circuit (computer) having a processor and a program-readable memory. The control portion 24 controls the endoscopic system 100 by executing an endoscope control program. The control portion 24 may include a dedicated circuit. The dedicated circuit is a processor separate from the processor of the control portion 24, a logic circuit implemented in an ASIC or FPGA, or a combination thereof.

The control portion 24 controls the illumination light source portion 21, the photoacoustic laser light source portion 22, and the transmission/reception portion 23. The control portion 24 also controls operation parameters and the like of the imaging portion 14, the illumination light irradiation portion 15, the laser light irradiation portion 16, and the ultrasonic probe 17 provided in the distal end rigid portion 11. The control portion 24 also instructs the image generation device 3 to generate an image and the display device 8 to display an image.

The recording portion 25 is a non-volatile recording medium that stores the above-described programs and necessary data. The recording portion 25 is composed of, for example, a flexible disk, a magneto-optical disk, a writable non-volatile memory such as a ROM or flash memory, a portable medium such as a CD-ROM, or a storage device such as a hard disk built into a computer system. Also, the recording portion 25 may be a storage device or the like provided on a cloud server connected to the control device 2 via the Internet.

[Image Generation Device 31]

The image generation device 3 is a device that generates an image based on data received from the imaging portion 14 and the ultrasonic probe 17 based on instructions from the control portion 24 of the control device 2. The image generation device 3 is a program-executable processing circuit (computer) having a processor and a program-readable memory or the like, a logic circuit implemented in an ASIC or FPGA, or a combination thereof.

The image generation device 3 may be configured as a device integrated with the control device 2. Further, the image generation device 3 may be an arithmetic device provided on a cloud server connected to the control device 2 via the Internet.

Figure 3:
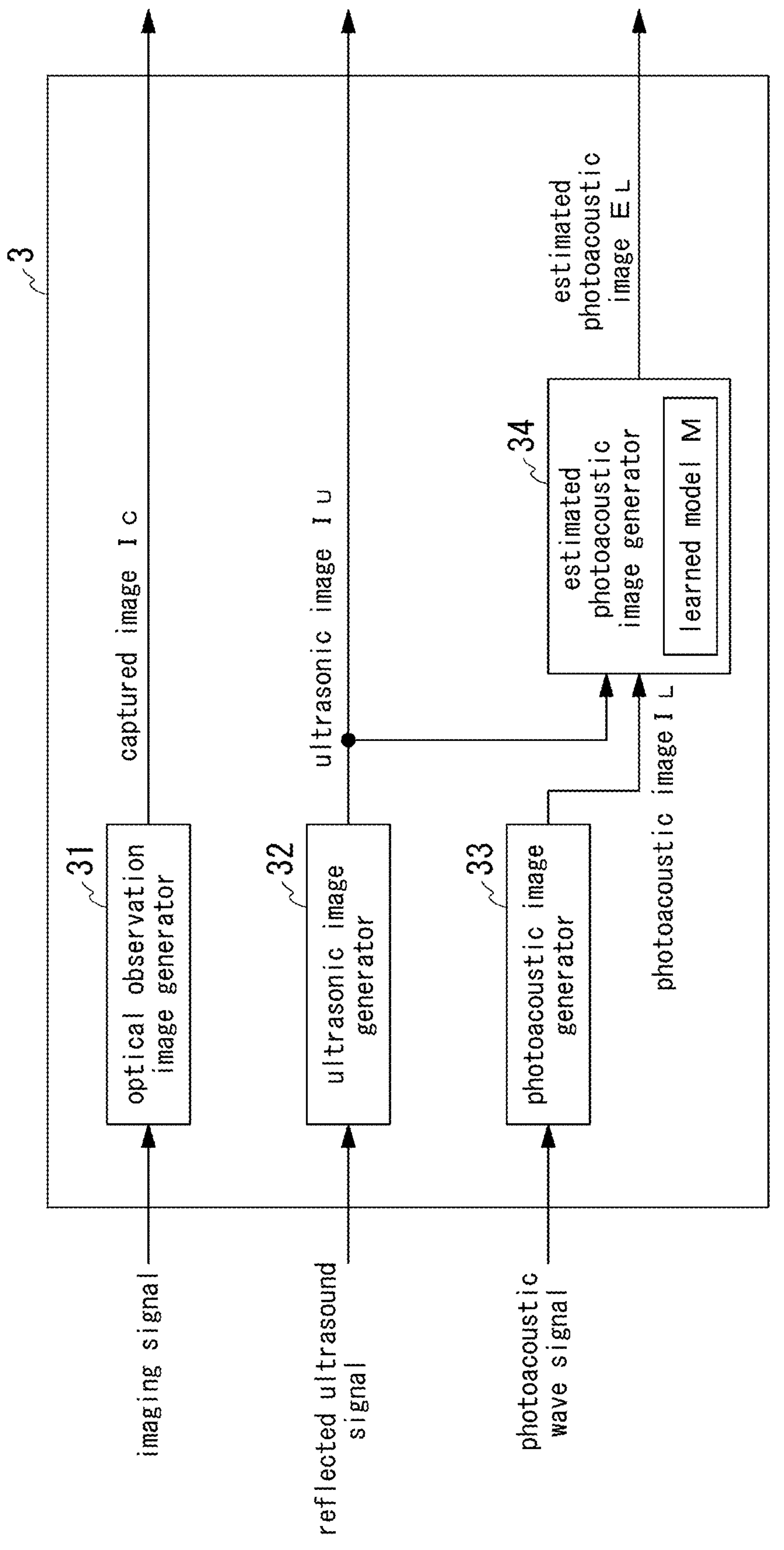
FIG. 3 is a functional block diagram of an image generation device of the endoscopic system.

FIG. 3 is a functional block diagram of the image generation device 3.

The image generation device 3 has an optical observation image generator 31, an ultrasonic image generator 32, a photoacoustic image generator 33, and an estimated photoacoustic image generator 34.

The optical observation image generator 31 processes the imaging signal received from the imaging portion 14 to generate a captured image Ic. The optical observation image generator 31 transmits the generated captured image Ic to the display device 8.

The ultrasonic image generator 32 processes the reflected ultrasound signal received from the transmission/reception portion 23 to generate an ultrasonic image IU. The ultrasonic image generator 32 transmits the generated ultrasonic image IU to the display device 8 and the estimated photoacoustic image generator 34.

The photoacoustic image generator 33 processes the photoacoustic wave signal received from the transmission/reception portion 23 to generate a photoacoustic image IL. The photoacoustic image generator 33 transmits the generated photoacoustic image IL to the estimated photoacoustic image generator 34.

The estimated photoacoustic image generator 34 generates an estimated photoacoustic image EL from the input ultrasonic image IU and the photoacoustic image IL based on a learned model M that has learned about the relationship between the ultrasonic image IU and the photoacoustic image IL.

Figure 4:
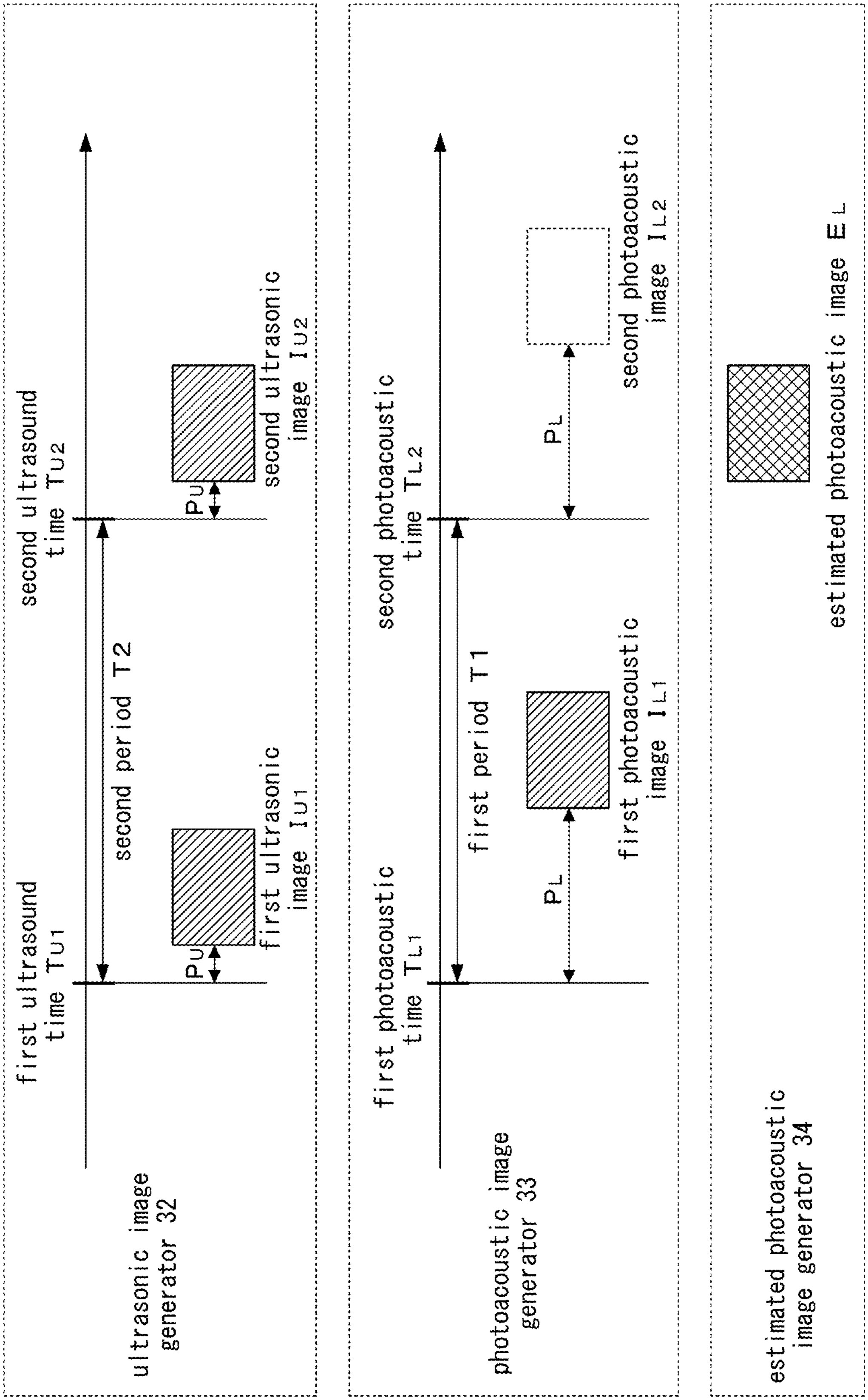
FIG. 4 is a diagram showing a relationship between ultrasonic images in the image generation device.

FIG. 4 is a diagram showing the relationship between the ultrasonic image IU and the photoacoustic image IL.

The photoacoustic image IL input to the estimated photoacoustic image generator 34 is a first photoacoustic image IL1. The first photoacoustic image IL1 is a photoacoustic image IL generated based on the photoacoustic wave signal obtained by observing the subject at a first photoacoustic time TL1. The estimated photoacoustic image EL estimated by the estimated photoacoustic image generator 34 is a photoacoustic image IL that estimates the subject at a second photoacoustic time TL2 after a first period T1 has elapsed from the first photoacoustic time TL1.

The ultrasonic images IU input to the estimated photoacoustic image generator 34 are a first ultrasonic image IU1 and a second ultrasonic image IU2. The first ultrasonic image IU1 is an ultrasonic image IU generated based on reflected ultrasound signals from which the subject was observed at a first ultrasound time TU1. The second ultrasonic image IU2 is an ultrasonic image IU generated based on reflected ultrasound signals obtained by observing the subject at a second ultrasound time TU2 after a second period T2 has elapsed from the first ultrasound time TU1.

Since the amount of photoacoustic wave information detected by the photoacoustic image generator 33 is enormous, it takes a certain amount of time to generate the photoacoustic image IL from the photoacoustic wave signal. As shown in FIG. 4, a time PL required for the photoacoustic image generator 33 to generate the photoacoustic image IL is longer than a time PU required for the ultrasonic image generator 32 to generate the ultrasonic image IU. Therefore, when simultaneously observing the ultrasonic image IU and the photoacoustic image IL generated based on the signal for observing the object at the same time, the user needs to wait until the photoacoustic image IL is generated.

Based on the learned model M, the estimated photoacoustic image generator 34 generates the estimated photoacoustic image EL from the input first ultrasonic image IU1, second ultrasonic image IU2, and first photoacoustic image IL1. The estimated photoacoustic image EL is a photoacoustic image IL obtained by estimating the subject at the second photoacoustic time TL2. The second photoacoustic time TL2 substantially coincides with the second ultrasonic time TU2, and desirably they coincide.

Before the second photoacoustic image IL2 actually generated based on the photoacoustic wave signal that observed the subject at the second photoacoustic time TL2 is output, as shown in FIG. 4, the user can observe the second ultrasound image IU2 and the estimated photoacoustic image EL.

The image generation device 3 may further include a composite image generator that combines the second ultrasonic image IU2 and the estimated photoacoustic image EL. The photoacoustic image IL is a cross-sectional image of a living body with higher resolution and contrast than the ultrasonic image IU. Therefore, the image generation device 3 may extract, for example, a thin blood vessel image that is easier to observe in the photoacoustic image IL and superimpose it on the ultrasonic image IU. The image generation device 3 can generate a composite image that takes advantage of both the photoacoustic image IL, which makes it easy to visualize the cross section of the living body with high resolution and contrast and obtains information on functions such as blood oxygen concentration as needed, and the ultrasonic image IU for easy visualization of metal treatment tools such as biopsy needles.

The image generation device 3 may output only the estimated photoacoustic image EL to the display device 8 and not output the ultrasonic image IU to the display device 8. That is, the image generation device 3 may use the ultrasonic image IU only as means for estimating the estimated photoacoustic image EL.

[Learned Model M]

The learned model M is a machine learning model that learns the relationship between an input image and an output image, and is a machine learning model suitable for image generation, such as a neural network, simple perceptron, or multi-layer perceptron. The learned model M is generated by prior learning based on teacher data. The learned model M may be generated by the image generation device 3 or by using another computer with higher computing power than the image generation device 3.

Figure 5:
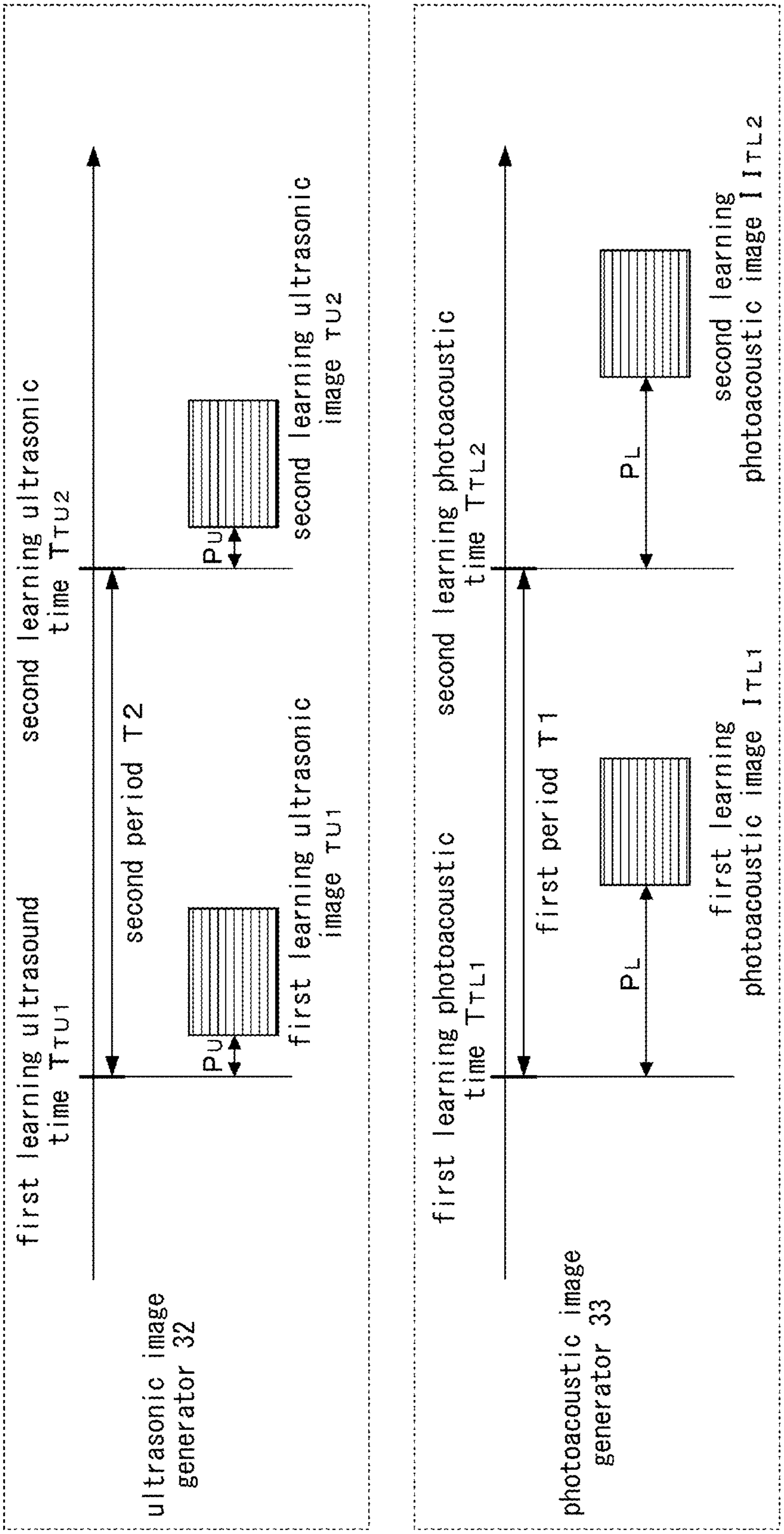
FIG. 5 is a diagram showing teacher data used for generating a learned model.

FIG. 5 is a diagram showing teacher data used to generate a learned model M.

The teacher data is an image group in which a first learning ultrasonic image ITU1, a second learning ultrasonic image ITU2, a first learning photoacoustic image ITL1, and a second learning photoacoustic image ITL2 are set as a set of images. It is desirable that the teacher data contain as many diverse images as possible.

The first learning photoacoustic image ITL1 is a photoacoustic image IL generated based on the photoacoustic wave signal obtained by observing the subject at a first learning photoacoustic time TTL1. The second learning photoacoustic image ITL2 is a photoacoustic image IL generated based on the photoacoustic wave signal obtained by observing the subject at a second learning photoacoustic time TTL2 after the first period T1 has elapsed from the first learning photoacoustic time TTL1. That is, the first learning photoacoustic image ITL1 and the second learning photoacoustic image ITL2 are photoacoustic images IL generated based on the photoacoustic wave signals obtained by observing the subject at intervals of the first period T1.

The first learning ultrasonic image ITU1 is an ultrasonic image IU generated based on an ultrasound signal obtained by observing the subject at a first learning ultrasound time TTU1. The second learning ultrasonic image ITU2 is an ultrasonic image IU generated based on an ultrasonic signal obtained by observing the subject at a second learning ultrasonic time TTU2 after the second period T2 has elapsed from the first learning ultrasonic time TTU1. That is, the first learning ultrasonic image ITU1 and the second learning ultrasonic image ITU2 are ultrasonic images IU generated based on ultrasonic signals obtained by observing the subject at intervals of the second period T2.

The second learning photoacoustic time TTL2 and the second learning ultrasonic time TTU2 in the teacher data approximately match, and it is desirable that they match. By matching the learning second photoacoustic time TTL2 and the learning second ultrasonic time TTU2 at the time of learning, the learned model M is more likely to be estimated as an estimated photoacoustic image EL in which the second photoacoustic time TL2 at the time of estimation matches the second ultrasonic time TU2.

Figure 6:
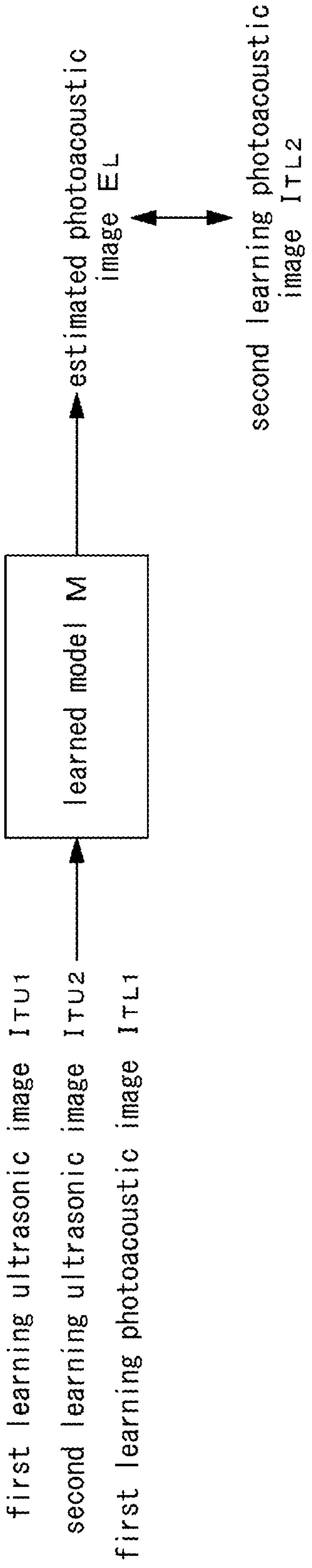
FIG. 6 is a diagram showing generation of a learned model.

FIG. 6 is a diagram explaining the generation of the learned model M.

The learned model M generates an estimated photoacoustic image EL based on the input first learning ultrasonic image ITU1, second learning ultrasonic image ITU2, and first learning photoacoustic image ITL1. The learned model M updates the parameters of the learned model M so that the difference between the output estimated photoacoustic image EL and the second learning photoacoustic image ITL2 is reduced.

It is desirable that the first period T1 and the second period T2 be the same as each other. This is because it is easier for the learned model M to efficiently learn the relationship between the ultrasonic image IU and the photoacoustic image IL when the first period T1 and the second period T2 are the same.

The first learning photoacoustic image ITL1 and the second learning photoacoustic image ITL2 prepared as learning data may be photoacoustic images IL generated based on photoacoustic wave signals obtained by observing the subject at intervals of the first period T1±error period. The above error period is acceptable as long as a learned model M capable of estimating the estimated photoacoustic image EL can be generated.

The first learning ultrasonic image ITU1 and the second learning ultrasonic image ITU2 prepared as learning data may be the ultrasound image IU generated based on ultrasound signals obtained by observing the subject at intervals of the second period T2± error period. The above error period is acceptable as long as a learned model M capable of estimating the estimated photoacoustic image EL can be generated.

[Operation of the Endoscopic System 100]

Next, the operation (image generation method, image generation program) of the image generation device 3 of the endoscopic system 100 will be described. Here, an operation example in which the endoscopic system 100 periodically generates the estimated photoacoustic image EL is shown.

Figure 7:
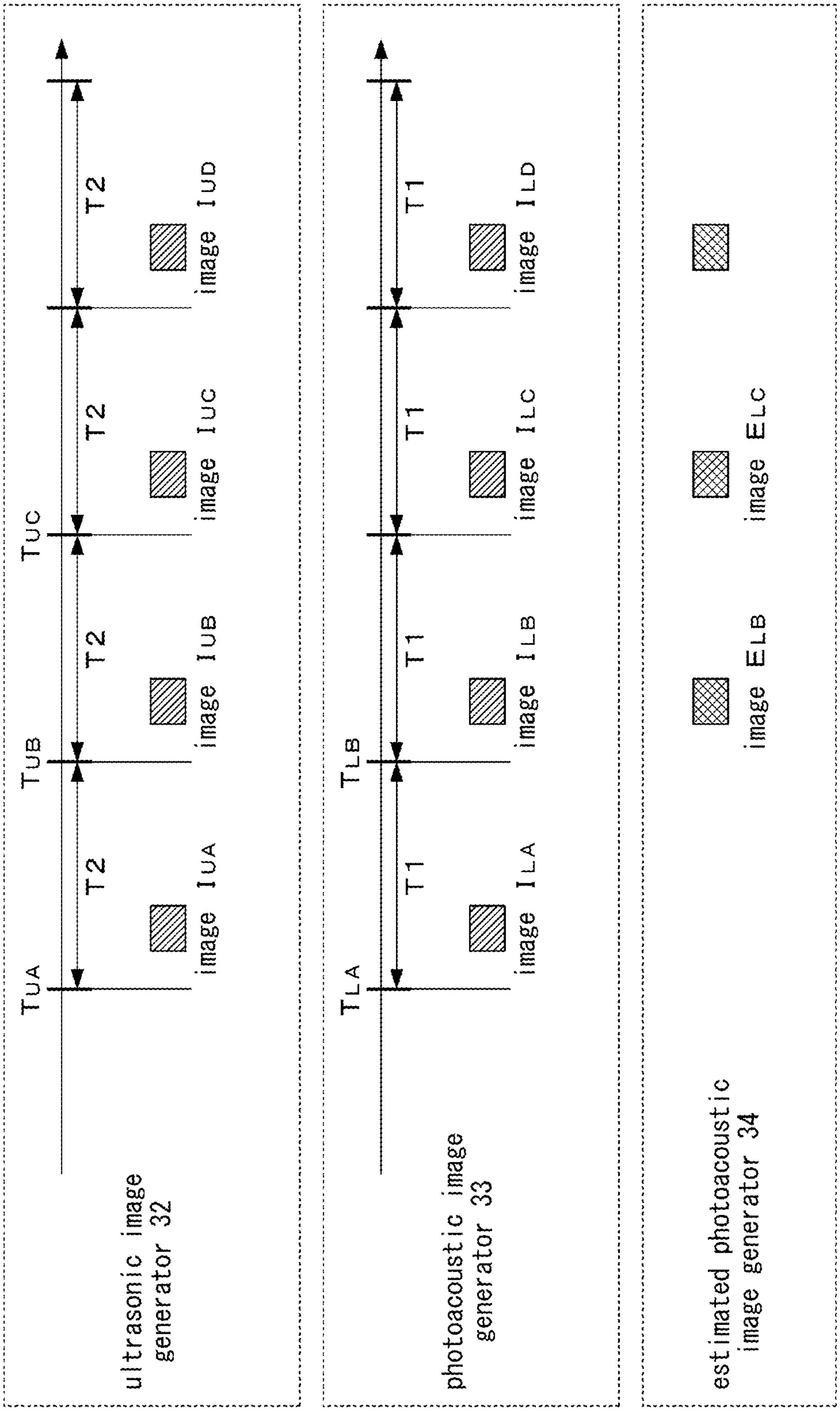
FIG. 7 is a diagram showing the operation of the image generation device.

FIG. 7 is a diagram showing the operation of the image generation device 3.

The image generation device 3 generates a photoacoustic image IL based on the photoacoustic wave signals obtained by observing the subject at intervals of the first period T1. The generated photoacoustic images IL are referred to as a photoacoustic image ILA, a photoacoustic image ILB, a photoacoustic image ILC, and a photoacoustic image ILD in chronological order, as shown in FIG. 7.

The photoacoustic image ILA is a photoacoustic image IL generated based on the photoacoustic wave signal that observed the subject at a photoacoustic time TLA.

The image generation device 3 generates the ultrasonic image IU based on ultrasound signals obtained by observing the subject at intervals of the second period T2. The generated ultrasonic images IU are referred to as an ultrasonic image IUA, an ultrasonic image TUB, an ultrasonic image IUC, and an ultrasonic image IUD in chronological order, as shown in FIG. 7.

The ultrasonic image IUA is an ultrasonic image IU generated based on the photoacoustic wave signal that observed the subject at an ultrasound time TUA. The ultrasonic time TUA substantially coincides with the photoacoustic time TLA.

The image generation device 3 converts the ultrasonic image IUA, the ultrasonic image IUB, and the photoacoustic image ILA into the first ultrasonic image IU1, the second ultrasonic image IU2, and the first photoacoustic image IL1, respectively, and the estimated photoacoustic image generator 34 generates an estimated photoacoustic image EL (estimated photoacoustic image ELB). The image generation device 3 outputs the ultrasonic image IUB and the estimated photoacoustic image ELB to the display device 8. The display device 8 displays the ultrasonic image IUB and the estimated photoacoustic image ELB having a small delay with respect to the photoacoustic image ILB.

Next, the image generation device 3 inputs the ultrasonic image IUB, the ultrasonic image IUC, and the photoacoustic image ILB as the first ultrasound image IU1, the second ultrasound image IU2, and the first photoacoustic image IL1, respectively, to the estimated photoacoustic image generator 34, to generate an estimated photoacoustic image EL (estimated photoacoustic image ELC). The image generation device 3 outputs the ultrasonic image IUC and the estimated photoacoustic image ELC to the display device 8. The display device 8 displays the ultrasonic image IUC and the estimated photoacoustic image ELC having a small delay with respect to the photoacoustic image ILC.

The image generation device 3 periodically generates the estimated photoacoustic image EL similarly thereafter. The image generation device 3 outputs the periodically generated estimated photoacoustic image EL to the display device 8.

According to the endoscopic system 100 according to this embodiment, the delay of the photoacoustic image with respect to the ultrasonic image can be reduced by generating the estimated photoacoustic image EL.

As described above, the first embodiment of the present invention has been described in detail with reference to the drawings, but the specific configuration is not limited to this embodiment, and design changes and the like are included within the scope of the present invention. Also, the constituent elements shown in the above-described embodiment and modification can be combined as appropriate.

(Modification 1)

In the above embodiment, the estimated photoacoustic image generator 34 generates an estimated photoacoustic image EL from the input first ultrasonic image IU1, second ultrasonic image IU2, and first photoacoustic image IL1, based on the learned model M learned about the relationship between the ultrasonic image IU and the photoacoustic image IL. However, the aspect of the estimated photoacoustic image generator 34 is not limited to this. The estimated photoacoustic image generator 34 may generate the estimated photoacoustic image EL by known image processing based on the first ultrasonic image IU1, the second ultrasonic image IU2, and the first photoacoustic image IL1.

(Modification 2)

Figure 8:
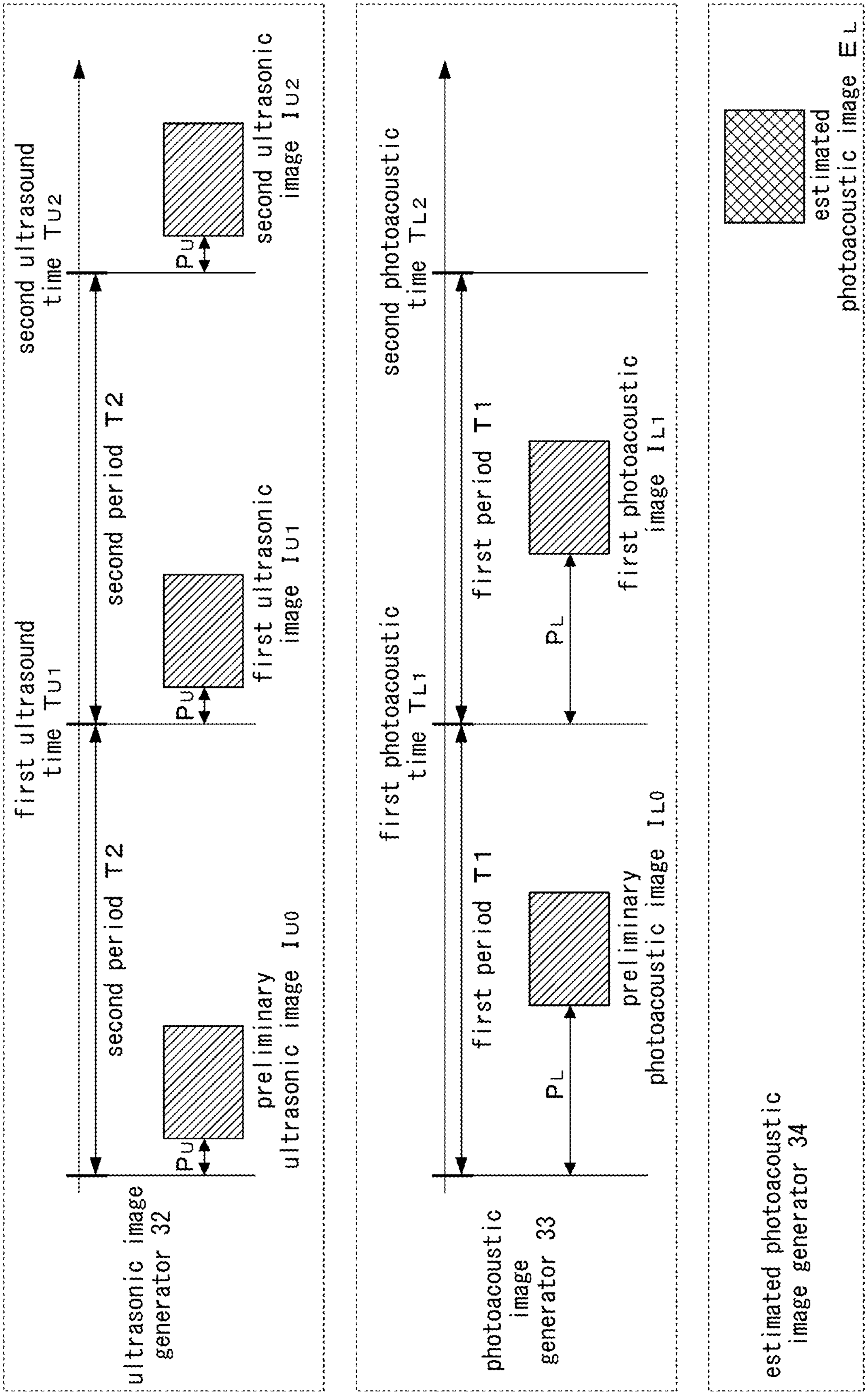
FIG. 8 is a diagram showing another aspect of generating an estimated photoacoustic image from an ultrasonic image and an ultrasonic image.

In the above embodiment, the estimated photoacoustic image generator 34 generates the estimated photoacoustic image EL from the first ultrasonic image IU1, the second ultrasonic image IU2, and the first photoacoustic image IL1. However, the aspect of the estimated photoacoustic image generator 34 is not limited to this. FIG. 8 is a diagram showing another aspect of generating an estimated photoacoustic image EL from an ultrasonic image and an ultrasonic image. The estimated photoacoustic image generator 34 may further input the preliminary ultrasonic image IU0 acquired before the first ultrasonic image IU1 and the preliminary photoacoustic image IL0 acquired before the first photoacoustic image IL1. In this case, the inputs used in training the learned model M are also changed accordingly. The estimated photoacoustic image generator 34 can estimate the estimated photoacoustic image EL more accurately by increasing the number of inputs.

Second Embodiment

An endoscopic system 100B according to a second embodiment of the present invention will be described with reference to FIGS. 9 to 10. In the following description, the same reference numerals are given to the same configurations as those already described, and redundant descriptions will be omitted. The endoscopic system 100B differs from the endoscopic system 100 according to the first embodiment in that the learned model M is re-learned.

The endoscopic system 100B includes an ultrasonic endoscope 1, a control device 2, an image generation device 3B, and a display device 8.

Figure 9:
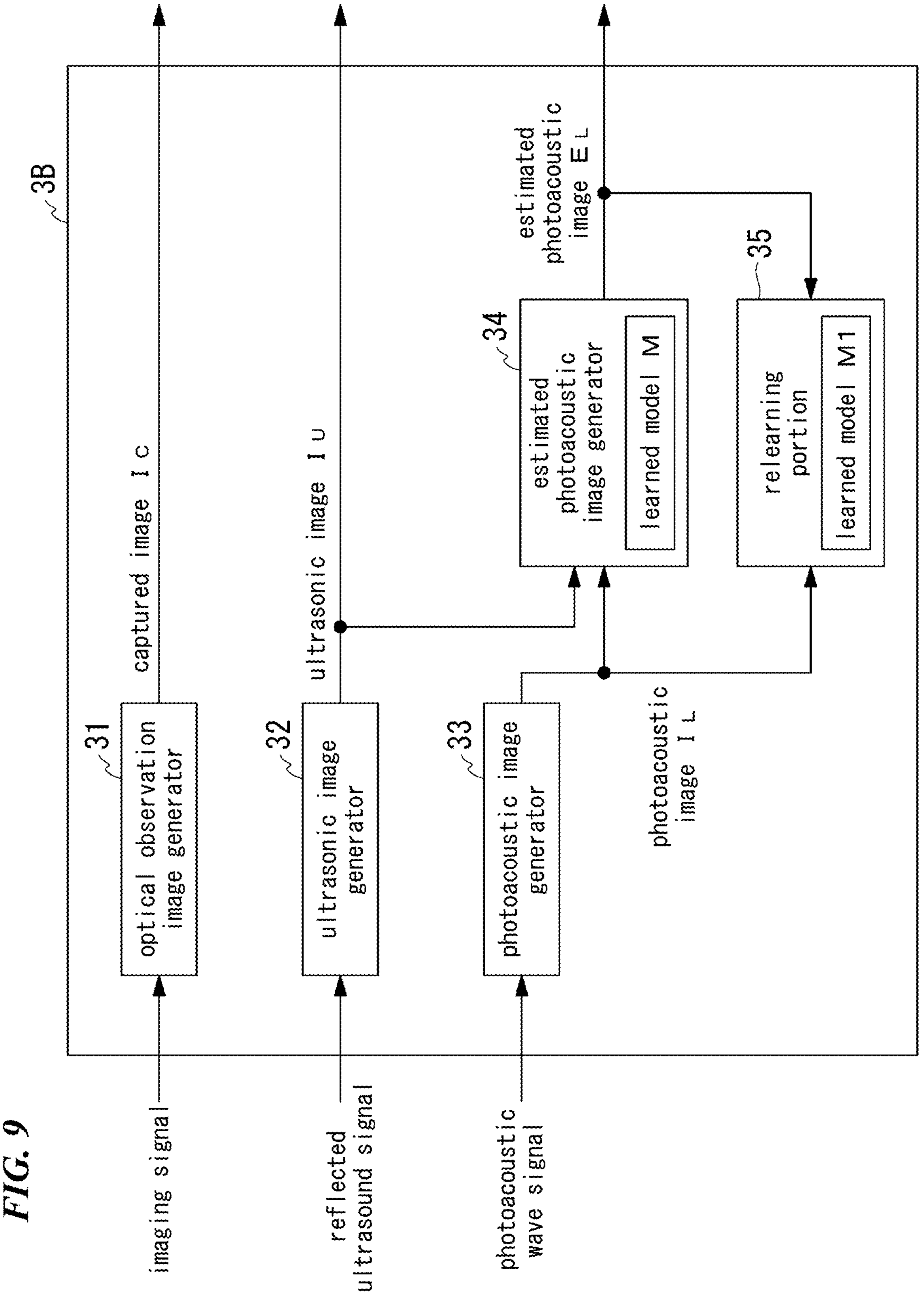
FIG. 9 is a functional block diagram of an image generation device of an endoscopic system according to a second embodiment.

FIG. 9 is a functional block diagram of the image generation device 3B.

The image generation device 3B has an optical observation image generator 31, an ultrasonic image generator 32, a photoacoustic image generator 33, an estimated photoacoustic image generator 34, and a relearning portion 35.

Figure 10:
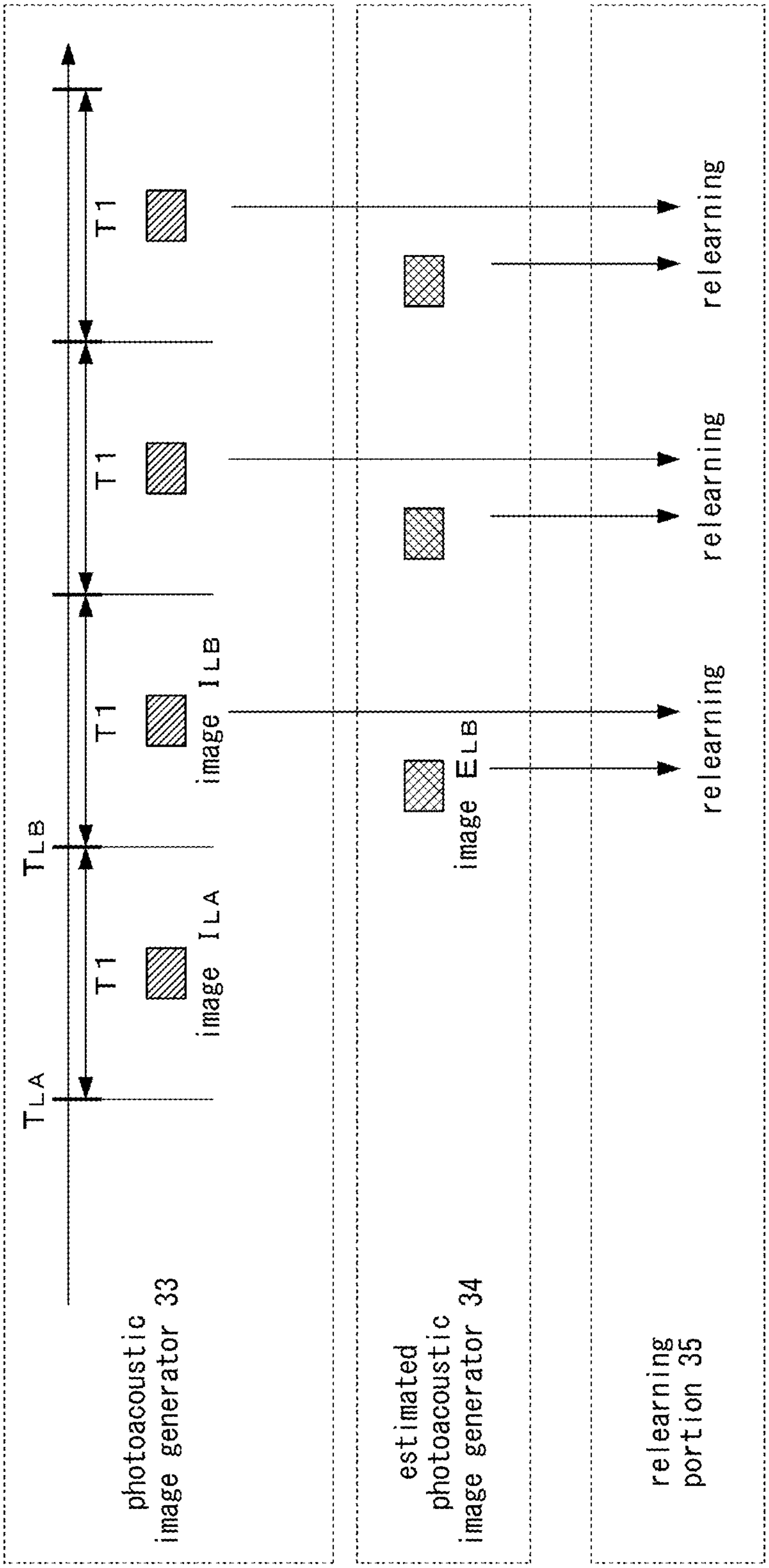
FIG. 10 is a diagram explaining the operation of the relearning portion of the image generation device.

FIG. 10 is a diagram explaining the operation of the relearning portion 35.

For example, the relearning portion 35 updates the learned model M to a learned model M1 by re-learning using the actually generated photoacoustic image ILB, based on the estimated photoacoustic image ELB, which is the photoacoustic image IL in which the subject is estimated at the photoacoustic time TLB, and the photoacoustic wave signal obtained by observing the subject at the photoacoustic time TLB. The learned model M is updated to the learned model M1 by re-learning using the photoacoustic image ILB obtained. The relearning portion 35 performs relearning every predetermined period. The relearning portion 35 replaces the learned model M of the estimated photoacoustic image generator 34 with the re-learned learned model M1 based on a predetermined condition.

The relearning portion 35 can also be used for performance evaluation of estimation of the estimated photoacoustic image EL by the image generation device 3B. The user may determine that the estimation accuracy of the learned model M is sufficient when the relearning by the relearning portion 35 is saturated.

According to the endoscopic system 100B according to the present embodiment, by generating the estimated photoacoustic image EL, the delay of the photoacoustic image with respect to the ultrasonic image can be reduced. The endoscopic system 100B can improve the estimation accuracy of the estimated photoacoustic image EL by re-learning the learned model M by comparing the generated estimated photoacoustic image EL and the photoacoustic image.

As described above, the second embodiment of the present invention has been described in detail with reference to the drawings, but the specific configuration is not limited to this embodiment, and design changes and the like are also included within the scope of the present invention. Also, the constituent elements shown in the above-described embodiments and modifications can be combined as appropriate.

The program in each embodiment may be recorded in a computer-readable recording medium, and the program recorded in this recording medium may be read into a computer system and executed. The "computer system" includes hardware such as an OS and peripheral devices. The term "computer-readable recording medium" refers to portable media such as flexible discs, magneto-optical discs, ROMs and CD-ROMs, and storage devices such as hard discs incorporated in computer systems. Furthermore, "computer-readable recording medium" refers to a program that dynamically retains programs for a short period of time, like a communication line when transmitting a program via a network such as the Internet or a communication line such as a telephone line. It may also include something that holds the program for a certain period of time, such as a volatile memory inside a computer system that serves as a server or client in that case. Further, the program may be for realizing some of the functions described above, or may be capable of realizing the functions described above in combination with a program already recorded in the computer system.

What is claimed is:

1. An image generation device comprising:

one or more processors comprising hardware, the one or more processors being configured to:

receive a first ultrasonic image generated based on a first reflected ultrasound signal obtained by observing a subject at a first ultrasound time;

generate a first photoacoustic image based on a first photoacoustic wave signal obtained by observing the subject at a first photoacoustic time;

generate a second photoacoustic image based on a second photoacoustic wave signal obtained by observing the subject at a second photoacoustic time after the first ultrasound time and after a first period elapsed from the first photoacoustic time; and generate, before generating the second photoacoustic image, an estimated photoacoustic image that estimates the subject at the second photoacoustic time based on the first photoacoustic image and the first ultrasonic image.

2. The image generation device according to claim 1, wherein the one or more processors are configured to generate the estimated photoacoustic image based on a learned model that has learned a relationship between the first ultrasonic image and the first photoacoustic image.

3. The image generation device according to claim 1, wherein:

the one or more processors are configured to receive a second ultrasonic image; and the second ultrasonic image is generated based on a second reflected ultrasonic signal obtained by observing the subject at a second ultrasonic time after a second period has elapsed from the first ultrasound time.

4. The image generation device according to claim 3, wherein:

the one or more processors are configured to generate the estimated photoacoustic image, based on a learned model that has learned a relationship between the first ultrasonic image and the first photoacoustic image by using a first learning ultrasonic image, a second learning ultrasonic image, a first learning photoacoustic image, and a second learning photoacoustic image;

the first learning photoacoustic image and the second learning photoacoustic image are photoacoustic images generated based on photoacoustic wave signals obtained by observing a learning subject at intervals of a first learning period; and the first learning ultrasonic image and the second learning ultrasonic image are ultrasonic images generated based on reflected ultrasonic signals obtained by observing the learning subject at intervals of a second learning period.

5. The image generation device according to claim 3, wherein the one or more processors are configured to generate the estimated photoacoustic image by image processing based on the first ultrasonic image, the second ultrasonic image, and the first photoacoustic image.

6. The image generation device according to claim 3, wherein the second photoacoustic time coincides with the second ultrasonic time.

7. The image generation device according to claim 3, wherein the first period coincides with the second period.

8. The image generation device according to claim 3, wherein:

the one or more processors are configured to generate a composite image based on the second ultrasonic image and the estimated photoacoustic image.

9. The image generation device according to claim 1, wherein:

the one or more processors are configured to generate a superimposed image based on the first ultrasonic image and the first photoacoustic image.

10. An endoscopic system comprising:

the image generation device according to claim 1; and an endoscope.

11. An image generation method comprising:

receiving a first ultrasonic image generated based on a first reflected ultrasound signal obtained by observing a subject at a first ultrasound time;

generating a first photoacoustic image based on a first photoacoustic wave signal obtained by observing the subject at a first photoacoustic time;

generating a second photoacoustic image based on a second photoacoustic wave signal obtained by observing the subject at a second photoacoustic time after the first ultrasound time and after a first period elapsed from the first photoacoustic time; and generating, before generating the second photoacoustic image, an estimated photoacoustic image that estimates the subject at the second photoacoustic time based on the first photoacoustic image and the first ultrasonic image.

12. The image generation method according to claim 11, wherein generating the estimated photoacoustic image comprises generating the estimated photoacoustic image based on a learned model that has learned a relationship between the first ultrasonic image and the first photoacoustic image.

13. The image generation method according to claim 11, wherein the image generation method further comprises:

receiving a second ultrasonic image, wherein the second ultrasonic image is generated based on a second reflected ultrasonic signal obtained by observing the subject at a second ultrasonic image after a second period has elapsed from the first ultrasound time.

14. The image generation method according to claim 13, comprising generating the estimated photoacoustic image, based on a learned model that has learned a relationship between the first ultrasonic image and the first photoacoustic image by using a first learning ultrasonic image, a second learning ultrasonic image, a first learning photoacoustic image, and a second learning photoacoustic image, wherein the first learning photoacoustic image and the second learning photoacoustic image are photoacoustic images generated based on photoacoustic wave signals obtained by observing a learning subject at intervals of a first learning period, and wherein the first learning ultrasonic image and the second learning ultrasonic image are ultrasonic images generated based on reflected ultrasonic signals obtained by observing the learning subject at intervals of a second learning period.

15. The image generation method according to claim 13, comprising generating the estimated photoacoustic image by image processing based on the first ultrasonic image, the second ultrasonic image, and the first photoacoustic image.

16. An image generation device comprising one or more processors comprising hardware, wherein the one or more processors are configured to:

generate a first ultrasonic image based on a first reflected ultrasound signal obtained by observing a subject at a first ultrasound time;

obtain a first photoacoustic image generated based on a first photoacoustic wave signal obtained by observing the subject at a first photoacoustic time;

obtain a second photoacoustic image generated based on a second photoacoustic wave signal obtained by observing the subject at a second photoacoustic time after the first ultrasound time and after a first period elapsed from the first photoacoustic time; and generate, before generating the second photoacoustic image, an estimated photoacoustic image that estimates the subject at the second photoacoustic time based on the first photoacoustic image and the first ultrasonic image.

17. The image generation device according to claim 16, wherein the one or more processors are configured to generate the estimated photoacoustic image based on a learned model that has learned a relationship between the first ultrasonic image and the first photoacoustic image.

18. The image generation device according to claim 16, wherein:

the one or more processors are configured to receive a second ultrasound image; and the second ultrasound image is generated based on a second reflected ultrasonic signal obtained by observing the subject at a second ultrasound time after a second period has elapsed from the first ultrasound time.

19. The image generation device according to claim 18, wherein:

the one or more processors are configured to generate the estimated photoacoustic image, based on a learned model that has learned a relationship between the first ultrasonic image and the first photoacoustic image by using a first learning ultrasound image, a second learning ultrasound image, a first learning photoacoustic image, and a second learning photoacoustic image;

the first learning photoacoustic image and the second learning photoacoustic image are photoacoustic images generated based on photoacoustic wave signals obtained by observing a learning subject at intervals of a first learning period; and the first learning ultrasound image and the second learning ultrasound image are ultrasound images generated based on reflected ultrasound signals obtained by observing the learning subject at intervals of a second learning period.

20. A learning model generation method comprising:

generating a learning model based on a plurality of teacher data comprising:

a first learning photoacoustic image generated based on a photoacoustic wave signal obtained by observing a learning subject at a first learning time;

a first learning ultrasound image generated based on a reflected ultrasound signal obtained by observing the learning subject observed at the first learning time;

a second learning photoacoustic image generated based on the photoacoustic wave signal obtained by observing the learning subject at a second learning time after the first learning time; and a second learning ultrasound image generated based on the reflected ultrasound signal obtained by observing the learning subject at the second learning time;

wherein the learning model is configured to:

receive inputs of:

a first photoacoustic image generated based on a photoacoustic wave signal obtained by observing a subject at a first time;

a first ultrasound image generated based on reflected ultrasound signal obtained by observing the subject observed at the first time; and a second ultrasound image generated based on reflected ultrasound signal obtained by observing the subject at a second time after a first period elapsed from the first time; and output an estimated photoacoustic image by estimating the subject at the second time based on the first photoacoustic image, the first ultrasound image and the second ultrasound image.

* * * * *